US007041849B2

(12) United States Patent
Yada et al.

(10) Patent No.: US 7,041,849 B2
(45) Date of Patent: May 9, 2006

(54) METHOD OF RECOVERING POLYMERIZATION INHIBITOR AND METHOD OF PRODUCING ACRYLIC ACID

(75) Inventors: Shuhei Yada, Yokkaichi (JP); Kenji Takasaki, Yokkaichi (JP); Yasushi Ogawa, Yokkaichi (JP); Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/845,571

(22) Filed: May 14, 2004

(65) Prior Publication Data

US 2004/0210085 A1  Oct. 21, 2004

Related U.S. Application Data

(63) Continuation of application No. PCT/JP02/12198, filed on Nov. 21, 2002.

(30) Foreign Application Priority Data

Nov. 22, 2001 (JP) ............................. 2001-357117

(51) Int. Cl.
C07C 51/42 (2006.01)
C07C 51/16 (2006.01)
(52) U.S. Cl. ..................... 562/600; 562/545
(58) Field of Classification Search ............ 562/545, 562/600
See application file for complete search history.

(56) References Cited

U.S. PATENT DOCUMENTS 3,086,046 A * 4/1963 von Kutepow et al. ...... 562/598
4,317,926 A   3/1982 Sato et al. ................... 562/532

FOREIGN PATENT DOCUMENTS

| EP | 0 887 334 | 12/1998 |
| JP | 54-52038 | 4/1979 |
| JP | 56-17331 | 4/1981 |
| JP | 2001-181233 | 7/2001 |

* cited by examiner

*Primary Examiner*—Cecilia J. Tsang
*Assistant Examiner*—Taylor Victor Oh
(74) *Attorney, Agent, or Firm*—Wenderoth, Lind & Ponack, L.L.P.

(57) ABSTRACT

In an acrylic acid production process which comprises the step of producing acrylic acid by catalytic vapor-phase oxidation of propane, propylene, and/or acrolein; and purifying the acrylic acid produced in the step of producing with distillation in the presence of the polymerization inhibitor for preventing polymerization of the acrylic acid, a viscosity at 20° C. of the bottoms which comprises the polymerization inhibitor, discharged in the step of purifying, is adjusted to 2 Pa·s (2,000 cP) or less and the polymerization inhibitor is extracted using an aqueous medium.

According to the method, in an acrylic acid production process, an extraction operation for recovery of the polymerization inhibitor can be continuously conducted in a stable manner.

23 Claims, 2 Drawing Sheets

METHOD OF RECOVERING POLYMERIZATION INHIBITOR AND METHOD OF PRODUCING ACRYLIC ACID

This application is a continuation of International Application No. PCT/JP02/12198 filed Nov. 21, 2002.

TECHNICAL FIELD

The present invention relates to a method of recovering a polymerization inhibitor used in a step of purifying in an acrylic acid production process, and also relates to a method of producing acrylic acid including the method of recovering.

BACKGROUND ART

Acrylic acid can be obtained by obtaining a gas comprising acrylic acid which is obtained by catalytic vapor-phase oxidation of propylene or the like, collecting the gas as an acrylic acid aqueous solution by a collection column, separating moisture and low-boiling fractions by distillation, and rectifying using a fractionating column, as a distillate.

Usually, at all of the steps after the step of collecting, a polymerization inhibitor is added for preventing polymerization of acrylic acid. Polymerization inhibitors generally used include: p-hydroquinone, p-methoxyphenol, phenothiazine, copper compounds such as alkyl copper carbamates and manganese compounds. Each of them has a boiling point higher than that of acrylic acid and is concentrated in the bottoms of the fractionating column.

The polymerization inhibitor is usually discarded together with a residual compound having a high boiling point after recovery of the acrylic acid oligomer in the bottoms by thermal decomposition. In recent years, however, several methods have been proposed for recovering and recycling a polymerization inhibitor in the bottoms of the fractionating column from the point of costs for the production of acrylic acid.

The conventional methods of recovering the polymerization inhibitors are, for example, as follows.

(1) Simple-recycling: The bottoms of a fractionating column, which contains a polymerization inhibitor and is generated in the process for producing an acrylate, is sent without modification to the step of purifying (JP 2001-181233 A).

(2) Distillation with evaporator: The bottoms of a fractionating column, which contains a polymerization inhibitor, is introduced into an evaporator and a fraction obtained by evaporation of the polymerization inhibitor using the evaporator is recycled in the step of purifying (JP 56-17331 B).

(3) Water extraction: The polymerization inhibitor is recovered from the fraction obtained in (2) by water extraction (JP 60-59889 B).

In those conventional methods of recovering polymerization inhibitors, no compounds other than polymerization inhibitors have been taken into consideration and thus there is a problem of contamination with impurities.

When the bottoms of the fractionating column or the bottoms of a thermal decomposer after thermal decomposition for decomposing the acrylic acid oligomer of the bottoms of the fractionating column is sent to the step of purifying, all impurities in the bottoms are circulated through the step of purifying. Therefore, the circulation is unrealistic because of an increase in the concentrations of impurities in the product.

Also, in the case of evaporating the polymerization inhibitor using an evaporator, an increase in load of the step of purifying at the time of circulation through the step of purifying or an increase in the concentrations of impurities in the product is brought because the most part of impurities having boiling points lower than that of a polymerization inhibitor are collected.

Also, in the case of recovering a polymerization inhibitor with water extraction, similar bad influences are brought because water-soluble impurities are collected simultaneously therewith.

Furthermore, the operations of the above (1) and (2) also had a problem of difficulty in stable continuous operation because a solution to be treated, which contains the polymerization inhibitor, has high viscosity, and in the operations, a lowering an ability of a device owing to its dirt and a blockage tend to occur.

DISCLOSURE OF THE INVENTION

The present invention has been completed in view of the above problems and in a method of recovering a polymerization inhibitor used in an acrylic acid production process, an object of the present invention is to provide a method of recovering a polymerization inhibitor, in which the deterioration of the quality of a product due to impurities accompanying with the polymerization inhibitor is prevented when the polymerization inhibitor is circulated through the acrylic acid production process while an extraction operation is continuously conducted in a stable manner.

Furthermore, another object of the present invention is to provide a method of producing acrylic acid, in which the deterioration of the quality of a product due to impurities accompanying a polymerization inhibitor is prevented when the polymerization inhibitor is circulated through the acrylic acid production process while an extraction operation at the time of recovering the polymerization inhibitor is continuously conducted in a stable manner.

The inventors of the present invention have conducted various studies to solve the above problems. As a result, the inventors have found out that it becomes possible to conduct an extraction operation in a stable manner by keeping the viscosity of a bottoms, which comprises the above polymerization inhibitor and is discharged after purification, within a predetermined range when the polymerization inhibitor is recovered from the bottoms by extraction using an aqueous medium, and it is effective to attain an improvement in extraction efficiency and to prevent contamination with impurities.

That is, the present invention is as follows.

(1) A method of recovering a polymerization inhibitor from a bottoms that comprises the polymerization inhibitor, the bottoms being discharged in the following step of purifying in an acrylic acid production process which comprises the steps of: producing acrylic acid by catalytic vapor-phase oxidation of propane, propylene, and/or acrolein; and purifying the acrylic acid produced in the step of producing with distillation in the presence of the polymerization inhibitor for preventing polymerization of the acrylic acid, wherein the viscosity at 20° C. of the bottoms is adjusted to 2 Pass (2,000 cP) or less and the polymerization inhibitor is extracted using an aqueous medium.

(2) The method according to the item (1), wherein the bottoms is heated before the polymerization inhibitor is extracted from the bottoms using the aqueous medium.

(3) The method according to the item (1) or (2), wherein the method further comprises the step of volatilizing at least a part of a volatile substance in an aqueous solution comprising the polymerization inhibitor obtained by extraction by heating and/or decompressing the aqueous solution.

(4) The method according to the item (3), wherein the method further comprises the step of heating a liquid after the volatilization of at least a part of the volatile substance in the presence of an acid catalyst, cooling the liquid after the heating, and subjecting the cooled liquid to solid-liquid separation.

(5) The method according to any one of the items (1) to (4), wherein the polymerization inhibitor extracted using the aqueous medium is recycled by sending to the acrylic acid production process.

(6) The method according to any one of the items (2) to (5), wherein the heating of the bottoms before the extraction of the polymerization inhibitor using the aqueous medium is for thermally decomposing an acrylic acid oligomer in the bottoms.

(7) A method of producing acrylic acid, which comprises the steps of: producing acrylic acid by catalytic vapor-phase oxidation of propane, propylene, and/or acrolein; and purifying the acrylic acid produced in the step of producing with distillation in the presence of a polymerization inhibitor for preventing polymerization of the acrylic acid, wherein the viscosity at 20° C. of the bottoms, which comprises the polymerization inhibitor and is discharged in the step of purifying, is adjusted to 2 Pa·s (2,000 cP) or less and the polymerization inhibitor is extracted from the bottoms using an aqueous medium.

(8) The method according to the item (7), wherein the bottoms discharged in the step of purifying is heated at a temperature in the range of 150 to 250° C. for 0.1 to 40 hours, an aqueous medium, which is 1.5 or more times as high as the bottoms in volume ratio, is contacted with the bottoms at 40° C. or higher to recover the polymerization inhibitor in the bottoms as an aqueous solution, and the aqueous solution is recycled in the polymerization inhibitor used in the step of purifying.

The method of recovering a polymerization inhibitor of the present invention is wherein the polymerization inhibitor is recovered from the bottoms, which comprises the polymerization inhibitor and is discharged from the step of purifying in the acrylic acid production process, by extraction using an aqueous medium. The extraction is carried out after the viscosity at 20° C. of the bottoms is adjusted to 2 Pa·S (2,000 cP) or less at the time of a recovery of the polymerization inhibitor.

The viscosity of the bottoms that comprises the polymerization inhibitor substantially depends on a trace amount of acrylic acid oligomer in the bottoms particularly under the condition of 90° C. or lower. The viscosity of the bottoms may vary significantly even though the concentrations of acrylic acid and a dimer thereof and impurities such as maleic acid are in the same order. This may lead to extreme difficulty in the transport or extraction operation of a liquid.

Therefore, in the present invention, the viscosity at 20° C. of the bottoms is adjusted to 2 Pa·S (2,000 cP) or less. A viscosity of the bottoms in excess of 2 Pa·S is undesirable because the device used for the extraction operation becomes dirty and blockage occurs in the device upon the extraction operation.

In the present invention, the "bottoms that comprises the polymerization inhibitor" means a bottoms discharged in the step of purifying in the acrylic acid production process. Preferably, it is a liquid obtained by heating the above bottoms for condensation and/or a bottoms after thermal-decomposition obtained by subjecting the acrylic acid oligomer in the bottoms to a thermal-decomposition treatment and then recovering acrylic acid as a distilled gas or a distillate. In addition, it is also possible to apply the method of the present invention to the bottoms that comprises a polymerization inhibitor and is generated from the step of purifying in the acrylate production process.

The viscosity at 20° C. of the bottoms can be adjusted to 2Pa·S (2,000 cP) or less by controlling the contents by ratio of acrylic acid and an oligomer thereof (mainly a dimer) in the bottoms, or by heating the bottoms to decompose the dimer mainly made of a Michael addition product of the acrylic acid.

It is preferable to use a condensed bottoms as the "bottoms that comprises the polymerization inhibitor" in terms of miniaturization of the device, recovery efficiency, and thermal load. However, when the heating concentration or the heating of the acrylic acid oligomer is excessively conducted, the viscosity may increase remarkably. Therefore, the extraction efficiency can be improved by providing the bottoms with a suitable viscosity by adjusting processing time and temperature. Specifically, the temperature and processing time for the bottoms are 150 to 250° C. for 0.1 to 40 hours, preferably 160 to 230° C. for 0.5 to 20 hours.

Examples of a method of measuring the viscosity at 20° C. include a method in which an oscillation-type viscometer is installed in a line which supplies the bottoms to a recovery tank.

Moreover, it is preferable to adjust the decomposition temperature in the case of a thermal-decomposition treatment together with the viscosity of the bottoms so that the boiling point under the ordinary pressure of the bottoms may become 160° C. or higher. If the boiling point of the bottoms becomes lower than 160° C., the formation of a two-liquid layer in a step of extracting becomes difficult.

Examples of the polymerization inhibitors to be used in the acrylic acid production process include, but not limited to, p-hydroquinone, p-methoxyphenol, phenothiazine, and copper- or manganese-containing compounds.

The production of acrylic acid is carried out by the conventional method.

The bottoms discharged in the step of purifying contains, but not specifically limited to, 30 to 70% by weight of acrylic acid and 10 to 45% by weight of acrylic acid dimer as main components.

Moreover, but not specifically limited to, the bottoms after the thermal decomposition contains, for example, the following compounds. In addition, although an acrylic acid oligomer is decomposed to generate acrylic acid, part of the acrylic acid may be sent as a distillate (or gas) to the step of purifying from a thermal decomposer.

6–20% by weight of acrylic acid, 15 to 35% by weight of acrylic acid dimer, 3 to 14% by weight of maleic acid, 1 to 5% by weight of hydroquinone, 0 to 3% by weight of p-methoxyphenol, and 0 to 4% by weight of phenothiazine.

The extraction in the present invention is carried out with an aqueous medium. The aqueous medium to be used may be water generated from the process for purifying acrylic acid, specifically a distilled-water from a dehydration distillation column, ejector wastewater, or wastewater generated from washing the devices, or may be one supplied newly.

The amount of the aqueous medium used for the extraction is preferably 1.5 to 3 times as high as the bottoms that comprises the polymerization inhibitor in volume ratio. If the amount is far fewer than 1.5 times as high as the volume of the bottoms, there is a tendency that a two-liquid layer is hardly formed and the extraction operation becomes hard. An excess amount of the aqueous medium is not economical because the efficiency is not improved and the device of a recovery tank becomes large, resulting in an increase in thermal load.

The extraction-operation temperature is preferably in the range of 40 to 60° C. If the temperature is low, operationality tends to get worse owing to an increase in the viscosity of the bottoms. On the other hand, if the temperature is high, the amount of the oil dissolved into the water layer increases. Thus, in the case that the obtained extraction water layer is sent to the step of purifying, an oil layer may separate as the temperature of the liquid falls by the time the extraction water layer is sent.

Examples of the polymerization inhibitor recovered by the extraction water layer by the extraction operation include phenol compounds such as hydroquinone and p-methoxyphenol and metal complexes such as those of copper and manganese, while poorly water-soluble compounds such as phenothiazine cannot be recovered.

A recovery tank can be used for the extraction and a shape of the recovery tank may be a plate- or packing-type extraction column, or may be an empty column which does not comprise interior materials.

FIG. 2 shows an example of the recovery tank used for the extraction operation of the present invention. A bottoms is supplied to the recovery tank from a bottoms-supplying line 1 and water is supplied from an aqueous-medium-supplying line 2 below the interface of an oil layer in an extraction tank. In addition, it is also a preferable embodiment to form a distribution nozzle 5 on a supply port of the bottoms-supplying line 1 to improve the extraction efficiency.

The temperature of the recovery tank may be adjusted by adjusting the temperatures of the bottoms-supplying line 1 and the aqueous-medium-supplying line 2 by heat exchangers or the like (not shown in the figure) provided on the respective supplying lines.

The water layer from which the extraction has been completed is recovered from a water-layer-extracting line 3, while the oil layer is extracted from an oil-layer-extracting line 4. In addition, it is preferable to form a baffle 6 to prevent the bottoms supplied from the bottoms-supplying line 1 from mixing within the water-layer-extracting line 3. In an extraction operation, the extraction efficiency becomes high as much as the residence time passes but the size of the recovery tank increases, so that a long residence time is not preferable in cost. In addition, the residence time is adjusted by the fluid volume (velocity) of the bottoms supplied, the aqueous medium supplied, the water layer extracted, and the oil layer.

Furthermore, in the present invention, it is preferable to further include the step of volatilizing at least a part of a volatile substance by heating and/or decompressing an aqueous solution that comprises a polymerization inhibitor obtained by extraction. Consequently, among the impurities in the bottoms, aldehydes, specifically furfural, benzaldehyde, and so on can be quantitatively removed together with a distillate by distilling a part of an extract.

As a method of heating and/or decompressing, it is preferable to distill off 10% by volume or more, preferably 20% by volume or more of the aqueous solution comprising the polymerization inhibitor obtained by the extraction.

Furthermore, it is preferable to further include the step of heating a liquid after the volatilization of at least a part of the volatile substance in the presence of an acid catalyst, cooling down, and performing solid-liquid separation. Maleic acid in the liquid after volatilization can be isomerized to fumaric acid by heating the liquid after volatilization in the presence of an acid catalyst, and then the liquid is cooled down to separate fumaric acid, allowing the fumaric acid to be removed by solid-liquid separation.

The isomerization of maleic acid can be performed by the conventional method. Specifically, hydrochloric acid or the like is used as an acid catalyst at a concentration of 0.002 to 3 mol/l to a recovered solution to be processed. After heating of the solution, fumaric acid is separated by cooling down the solution to 10 to 40° C. and solid-liquid separation is carried out by filtration or the like, resulting in the finally-recovered liquid. Furthermore, after treating with the acid catalyst, it is also preferable to increase the amount of the separated fumaric acid together with the removal of hydrochloric acid by concentration.

Hereinafter, one of the embodiments of the present invention will be described. However, the present invention is not limited to that.

FIG. 1 is a flow diagram showing one of the embodiments of the present invention.

A bottoms from a thermal decomposer, which comprises a polymerization inhibitor, is supplied together with an aqueous medium used for extraction to a recovery tank for the extraction. In addition, instead of the bottoms, it is also possible to supply a bottoms from a purification column to the recovery tank. At this time, the viscosity at 20° C. of the bottoms supplied to the recovery tank is adjusted to 2 Pa·s or less. When a thermal-decomposition treatment is carried out in order to decompose the acrylic acid oligomer in the bottoms that comprises the polymerization inhibitor, it is preferable to subject the bottoms to the thermal-decomposition treatment with the thermal decomposer before supplying the bottoms to the recovery tank.

Subsequently, a water layer (an upper layer) is supplied to a heating tank for removal of aldehyde to carry out heating and decompressing. For removing maleic acid, an acid catalyst is added to an aqueous solution obtained by the heating and/or decompressing, and then the aqueous solution is heated to allow the isomerization of maleic acid to fumaric acid, transferred to a setting tank, and cooled to allow solid-liquid separation.

An acid catalyst is added to the extract obtained in the recovery tank, and then heating and concentration are carried out on the extract to simultaneously conduct the steps (removal of aldehyde and removal of maleic acid) performed in the heating tank and the setting tank.

The aqueous solution that comprises the polymerization inhibitor obtained from those steps can be recycled by the acrylic acid production process, specifically by sending the solution to the step of collecting acrylic acid.

BEST MODE FOR CARRYING OUT THE INVENTION

Figure 1:
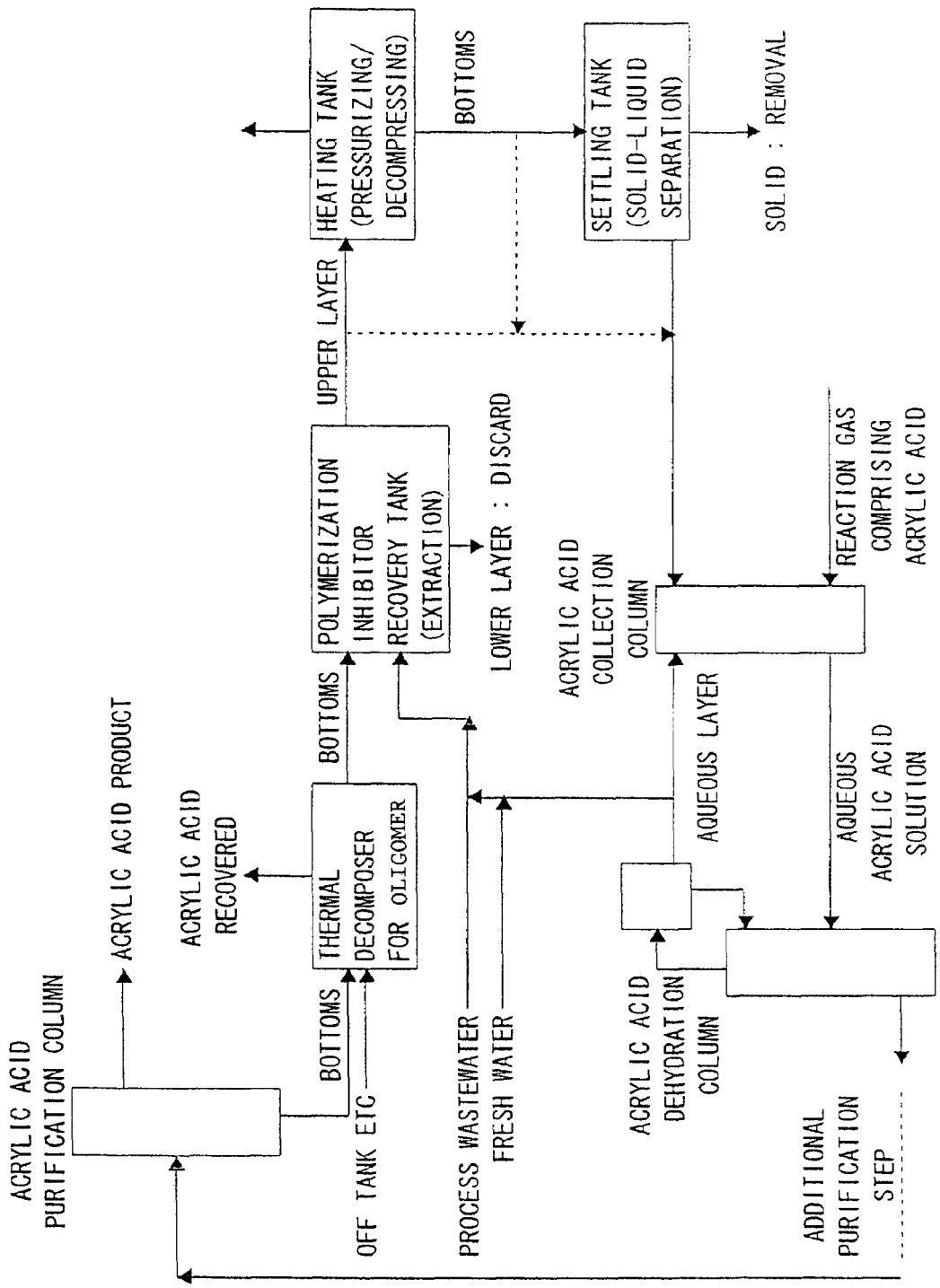
FIG. 1 is a flow diagram that illustrates one of the embodiments of a method of recovering a polymerization inhibitor of the present invention.
Figure 2:
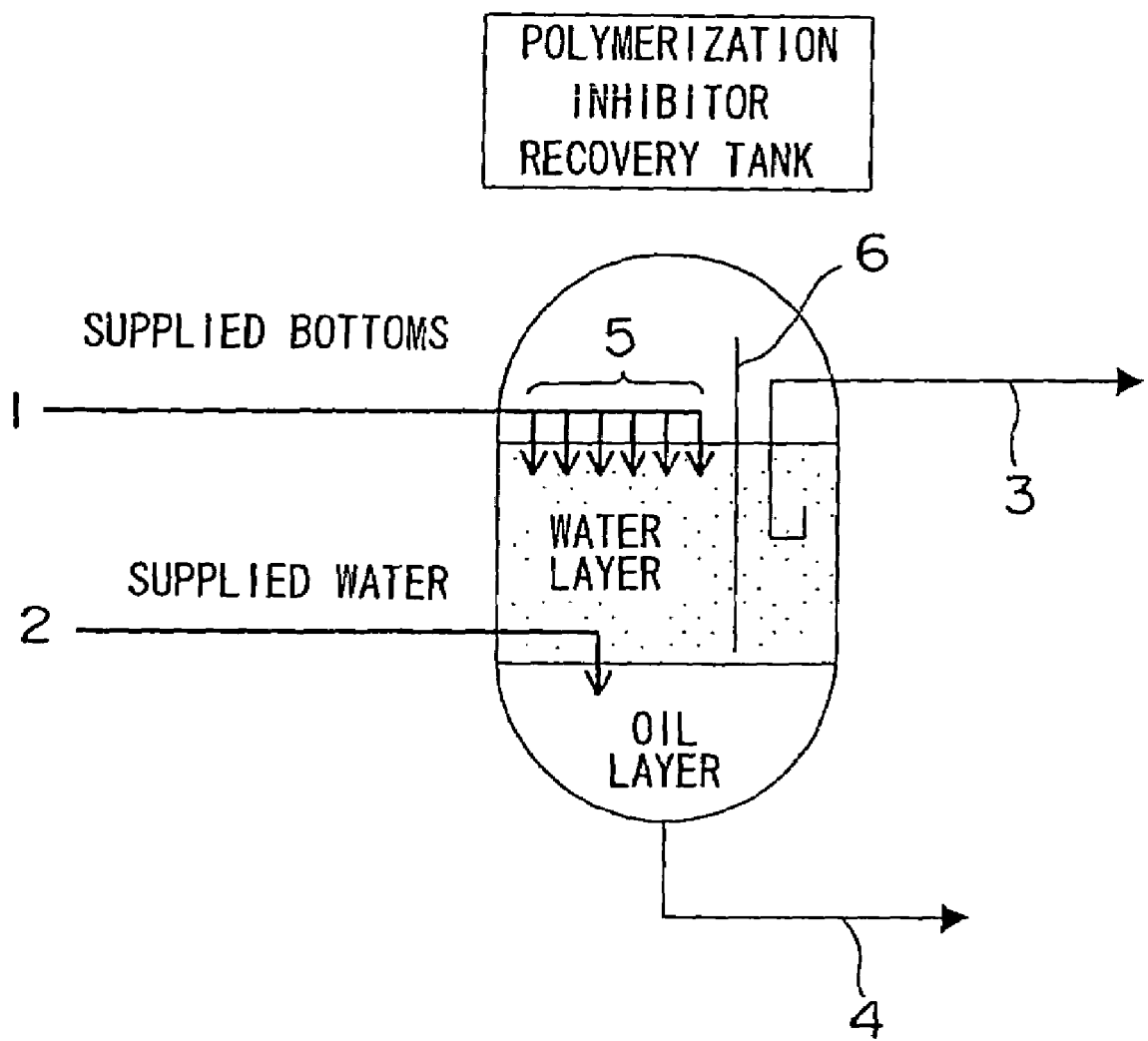
FIG. 2 is a diagram that illustrates a recovery tank used for the method of recovering a polymerization inhibitor of the present invention.

Hereinafter, the present invention will be described more concretely with reference to examples and comparative examples. However, the present invention is not limited to the following examples as far as within the gist of the present invention.

EXAMPLE 1

<Composition of Bottoms>

A bottoms of a purification column was subjected to a thermal-decomposition treatment for one hour using a thermal decomposer under the conditions of 200° C. and 100 kPa to obtain a gas comprising the recovered acrylic acid from the top of the thermal decomposer and a concentrated liquid comprising a polymerization inhibitor from the bottom of the thermal decomposer. The composition of the bottoms was as follows and the viscosity of the bottoms was 1.3 Pa·s/20° C.

| | |
|---|---|
| Acrylic acid | 16.4% by weight |
| Acrylic acid dimer | 15.6% by weight |
| Acrylic acid trimer | 7.1% by weight |
| Furfural | 690 ppm by weight |
| Benzaldehyde | 2,800 ppm by weight |
| Maleic acid | 4.3% by weight |
| p-hydroquinone | 1.8% by weight |
| p-methoxyphenol | 1.2% by weight |

<Operation 1> Water Extraction

Extraction was performed on the bottoms having the above composition under the following conditions. In addition, a water layer obtained by the extraction operation is 3.1 times as high as the bottoms in volume.

Operation temperature: 50° C., normal pressure
Supplied aqueous medium: water (distilled water)
Supplied aqueous medium/bottoms (volume ratio)=3
Average residence time in the recovery tank: 1 hour
Recovery tank: vertically cylindrical container with a length-to-width ratio=3
Insertion in the recovery tank: nothing
Upper layer (water layer): continuous extraction
Lower layer (oil layer): intermittent extraction every 10 minutes The compositions of a polymerization inhibitor and main impurities in the water layer obtained by the above extraction operation (hereinafter, referred to as an "extract") are as follows. In each parenthesis, a recovery rate is represented.

| | |
|---|---|
| Furfural | 145 ppm by weight (65%) |
| Benzaldehyde | 343 ppm by weight (38%) |
| Maleic acid | 0.79% by weight (57%) |
| p-hydroquinone | 0.40% by weight (69%) |
| p-methoxyphenol | 0.21% by weight (53%) |

<Operation 2> Distillation of Aldehyde

The extract obtained in the above Operation 1 was concentrated to 45% in volume under normal pressure. The composition of the resulting concentrated liquid is shown below. In each parenthesis, a recovery rate is represented.

| | |
|---|---|
| Furfural | 17 ppm by weight (3.5%) |
| Benzaldehyde | 1 ppm by weight (0.05%) |
| Maleic acid | 1.78% by weight (58%) |

| | |
|---|---|
| p-hydroquinone | 0.89% by weight (69%) |
| p-methoxyphenol | 0.45% by weight (52%) |

<Operation 3> Removal and Isomerization of Maleic Acid

Hydrochloric acid was added to the concentrated liquid which was obtained in the above Operation 2, and then the whole was stirred at 70° C. for 30 minutes, followed by heating to remove the hydrochloric acid while concentrating the liquid to ⅓ in volume. Subsequently, after the liquid had been cooled down to 30° C., the separated solid (a mixed crystal of fumaric acid and maleic acid) was isolated.

The composition of the resulting solution is shown below and in Table 1. In each parenthesis, a recovery rate is represented.

| | |
|---|---|
| Maleic acid + Fumaric acid | 1.75% by weight (19%) |
| p-hydroquinone | 2.43% by weight (63%) |
| p-methoxyphenol | 1.11% by weight (43%) |

COMPARATIVE EXAMPLE 1

A bottoms having the following composition and a viscosity of 2.2 Pa·s/20° C. was obtained by the same way as that of Example 1, except that the time for the thermal decomposition treatment was set to 1.2 hours. Operation 1 was performed on the bottoms by the same way as that of Example 1. The concentration of hydroquinone in the extract was 0.11% by weight (a recovery rate of 19%). The results obtained are shown in Table 1.

| | |
|---|---|
| Acrylic acid | 15.8% by weight |
| Acrylic acid dimer | 15.5% by weight |
| Acrylic acid trimer | 7.4% by weight |
| Furfural | 670 ppm by weight |
| Benzaldehyde | 2,800 ppm by weight |
| Maleic acid | 4.4% by weight |
| p-hydroquinone | 1.8% by weight |
| p-methoxyphenol | 1.1% by weight |

COMPARATIVE EXAMPLE 2

The bottoms obtained in Comparative Example 1 and having a viscosity of 2.2 Pa·s/20° C. was subjected to the same procedures as those of the example, except that the extraction operation was carried out at 60° C. The resulting concentration of hydroquinone in the extract was 0.15% by weight (a recovery rate of 27%). The results obtained are shown in Table 1.

EXAMPLE 2

Example 2 was performed by the same way as that of Operation 1 of Example 1, except that the water layer (comprising 6% by weight of acetic acid) of a bottoms of a dehydrating distillation column was used as a supplied aqueous medium in the extraction operation of Example 1. The concentration of hydroquinone in the extract was 0.35% by weight (a recovery rate of 61%), so that almost the same volume was recovered. The results obtained are shown in Table 1.

EXAMPLE 3

The polymerization inhibitor was recovered by the same way as that of Example 1, except that the temperature of the extraction operation was set to 60° C. in Operation 1 of Example 1. The concentration of hydroquinone in the extract was 0.40% by weight (a recovery rate of 71%). The results obtained are shown in Table 1.

TABLE 1

|  |  | Bottoms | Operation 1 | | Operation 2 | | Operation 3 | |
|---|---|---|---|---|---|---|---|---|
|  |  | Concentration (%) | Concentration (%) | Recovery (%) | Concentration (%) | Recovery (%) | Concentration (%) | Recovery (%) |
| Example 1 | Furfural | 0.069 | 145 ppm | 65 | 17 ppm | 3.5 | | |
|  | Benzaldehyde | 0.28 | 343 ppm | 38 | 1 ppm | 0.05 | | |
|  | Maleic acid | 4.3 | 0.79 | 57 | 1.78 | 58 | 1.75 | 19 |
|  | p-hydroquinone | 1.8 | 0.40 | 69 | 0.89 | 69 | 2.43 | 63 |
|  | p-methoxyphenol | 1.2 | 0.21 | 53 | 0.45 | 52 | 1.11 | 43 |
| Example 2 | Furfural | Same as | 151 ppm | 68 | | | | |
|  | Benzaldehyde | Example 1 | 352 ppm | 39 | | | | |
|  | Maleic acid | | 0.77 | 55 | | | | |
|  | p-hydroquinone | | 0.35 | 61 | | | | |
|  | p-methoxyphenol | | 0.21 | 53 | | | | |
| Example 3 | Furfural | Same as | 162 ppm | 75 | 20 ppm | 4.2 | | |
|  | Benzaldehyde | Example 1 | 403 ppm | 46 | 1 ppm | 0.06 | | |
|  | Maleic acid | | 0.99 | 74 | 2.18 | 73 | 2.23 | 26 |
|  | p-hydroquinone | | 0.40 | 71 | 0.89 | 71 | 2.40 | 64 |
|  | p-methoxyphenol | | 0.20 | 54 | 0.44 | 53 | 1.03 | 41 |
| Comparative Example 1 | Furfural | 0.067 | 140 ppm | 65 | | | | |
|  | Benzaldehyde | 0.28 | 289 ppm | 32 | | | | |
|  | Maleic acid | 4.4 | 0.79 | 56 | | | | |
|  | p-hydroquinone | 1.8 | 0.11 | 19 | | | | |
|  | p-methoxyphenol | 1.1 | 0.05 | 13 | | | | |
| Comparative Example 2 | Furfural | Same as | 155 ppm | 79 | 20 ppm | 4.2 | | |
|  | Benzaldehyde | Comparative | 341 ppm | 39 | 1 ppm | 0.06 | | |
|  | Maleic acid | Example 1 | 1.02 | 74 | 2.23 | 73 | 2.20 | 24 |
|  | p-hydroquinone | | 0.15 | 27 | 0.34 | 27 | 0.90 | 24 |
|  | p-methoxyphenol | | 0.06 | 18 | 0.13 | 17 | 0.34 | 15 |

INDUSTRIAL APPLICABILITY

According to the present invention, in the method of recovering a polymerization inhibitor used in an acrylic acid production process, an extraction operation can be continuously conducted in a stable manner. In addition, it is possible to provide a method of recovering a polymerization inhibitor in which the deterioration of the quality of a product due to impurities accompanying the polymerization inhibitor is prevented when the polymerization inhibitor is circulated through the acrylic acid production process.

Furthermore, according to the present invention, there can be provided a method of producing acrylic acid, in which the deterioration of the quality of a product due to impurities accompanying a polymerization inhibitor is prevented when the polymerization inhibitor is circulated through the acrylic acid production process while an extraction operation at the time of recovering the polymerization inhibitor is continuously conducted in a stable manner.

The invention claimed is:

1. A method of recovering a polymerization inhibitor from a liquid that comprises the polymerization inhibitor,
the liquid being discharged in an acrylic acid production process,
the acrylic acid producing process comprising the steps of: producing acrylic acid by catalytic vapor-phase oxidation of propane, propylene, and/or acrolein; and purifying the acrylic acid produced in the step of producing with distillation in the presence of the polymerization inhibitor for preventing polymerization of the acrylic acid,
the liquid being a residue discharged in the step of purifying,
wherein the method comprises the steps of:
adjusting a viscosity at 20° C. of the liquid to 2Pa·s (2,000 cP) or less; and
extracting the polymerization inhibitor from the liquid by using an aqueous medium.

2. The method according to claim 1, wherein the method further comprises the step of heating the liquid before extracting the polymerization inhibitor from the liquid by using the aqueous medium.

3. The method according to claim 1, wherein the method further comprises the step of volatilizing at least a part of a volatile substance in an aqueous solution comprising the polymerization inhibitor obtained by extraction by heating and/or decompressing the aqueous solution.

4. The method according to claim 2, wherein the method further comprises the step of volatilizing at least a part of a volatile substance in an aqueous solution comprising the polymerization inhibitor obtained by extraction by heating and/or decompressing the aqueous solution.

5. The method according to claim 3, wherein the method further comprises the step of heating a liquid after the volatilization of at least a part of the volatile substance in the presence of an acid catalyst, cooling the liquid after the heating, and subjecting the cooled liquid to solid-liquid separation.

6. The method according to claim 4, wherein the method further comprises the step of heating a liquid after the volatilization of at least a part of the volatile substance in the presence of an acid catalyst, cooling the liquid after the heating, and subjecting the cooled liquid to solid-liquid separation.

7. The method according to claim 1, wherein the method further comprises the step of recycling the polymerization inhibitor extracted by using the aqueous medium by sending the extracted inhibitor to the acrylic acid production process.

8. The method according to claim 2, wherein the method further comprises the step of recycling the polymerization inhibitor extracted by using the aqueous medium by sending the extracted inhibitor to the acrylic acid production process.

9. The method according to claim 3, wherein the method further comprises the step of recycling the polymerization inhibitor extracted by using the aqueous medium by sending the extracted inhibitor to the acrylic acid production process.

10. The method according to claim 4, wherein the method further comprises the step of recycling the polymerization inhibitor extracted by using the aqueous medium by sending the extracted inhibitor to the acrylic acid production process.

11. The method according to claim 5, wherein the method further comprises the step of recycling the polymerization inhibitor extracted by using the aqueous medium by sending the extracted inhibitor to the acrylic acid production process.

12. The method according to claim 6, wherein the method further comprises the step of recycling the polymerization inhibitor extracted by using the aqueous medium by sending the extracted inhibitor to the acrylic acid production process.

13. The method according to claim 2, wherein the heating of the liquid before the extraction of the polymerization inhibitor using the aqueous medium is for thermally decomposing an acrylic acid oligomer in the liquid.

14. The method according to claim 3, wherein the heating of the liquid before the extraction of the polymerization inhibitor using the aqueous medium is for thermally decomposing an acrylic acid oligomer in the liquid.

15. The method according to claim 4, wherein the heating of the liquid before the extraction of the polymerization inhibitor using the aqueous medium is for thermally decomposing an acrylic acid oligomer in the liquid.

16. The method according to claim 5, wherein the heating of the liquid before the extraction of the polymerization inhibitor using the aqueous medium is for thermally decomposing an acrylic acid oligomer in the liquid.

17. The method according to claim 6, wherein the heating of the liquid before the extraction of the polymerization inhibitor using the aqueous medium is for thermally decomposing an acrylic acid oligomer in the liquid.

18. The method according to claim 7, wherein the heating of the liquid before the extraction of the polymerization inhibitor using the aqueous medium is for thermally decomposing an acrylic acid oligomer in the liquid.

19. The method according to claim 8, wherein the heating of the liquid before the extraction of the polymerization inhibitor using the aqueous medium is for thermally decomposing an acrylic acid oligomer in the liquid.

20. The method according to claim 9, wherein the heating of the liquid before the extraction of the polymerization inhibitor using the aqueous medium is for thermally decomposing an acrylic acid oligomer in the liquid.

21. The method according to claim 10, wherein the heating of the liquid before the extraction of the polymerization inhibitor using the aqueous medium is for thermally decomposing an acrylic acid oligomer in the liquid.

22. The method according to claim 11, wherein the heating of the liquid before the extraction of the polymerization inhibitor using the aqueous medium is for thermally decomposing an acrylic acid oligomer in the liquid.

23. The method according to claim 12, wherein the heating of the liquid before the extraction of the polymerization inhibitor using the aqueous medium is for thermally decomposing an acrylic acid oligomer in the liquid.

* * * * *